United States Patent [19]

Healey et al.

[11] Patent Number: 5,425,918
[45] Date of Patent: Jun. 20, 1995

[54] APPARATUS FOR AUTOMATIC TISSUE STAINING FOR IMMUNOHISTOCHEMISTRY

[75] Inventors: Kevin Healey, Essendon; Graham L. Baxter, Fairfield, both of Australia

[73] Assignee: Australian Biomedical Corporation, Mt. Waverly, Australia

[21] Appl. No.: 151,826

[22] Filed: Nov. 15, 1993

Related U.S. Application Data

[62] Division of Ser. No. 960,358, Jan. 19, 1993.

[30] Foreign Application Priority Data

Jul. 18, 1990 [AU] Australia ............... PK 1231

[51] Int. Cl.⁶ .............................................. G01N 1/31
[52] U.S. Cl. ..................................... 422/64; 422/100; 435/288; 239/472
[58] Field of Search ............... 422/63, 64, 100; 436/43, 45, 46, 54, 180, 518–522; 239/590, 472, 491, 553; 435/288, 292, 287

[56] References Cited

U.S. PATENT DOCUMENTS

| | | | |
|---|---|---|---|
| 2,806,741 | 9/1957 | Fishelson et al. | 239/590 X |
| 3,368,872 | 2/1968 | Natelson | 422/66 |
| 3,574,064 | 4/1971 | Binnings et al. | 435/293 |
| 4,613,079 | 9/1986 | Mains . | |
| 4,801,093 | 1/1989 | Brunet et al. | 239/490 |
| 4,837,159 | 6/1989 | Yamada | 436/45 |
| 4,847,208 | 7/1989 | Bogen | 436/174 |
| 5,231,029 | 7/1993 | Wootton et al. | 435/289 |

Primary Examiner—Jeffrey R. Snay
Attorney, Agent, or Firm—Cushman Darby & Cushman

[57] ABSTRACT

Apparatus (10) for the automatic staining of tissue includes a body (12) on which a carousel (16) rotates. The carousel (16) is able to carry a number of slides (24) bearing tissue samples. A delivery head assembly (18) is mounted on the body (12) for movement across the diameter of the carousel (16). The head assembly contains a clear nozzle (20) and a spray nozzle (22). A version (50) of the spray nozzle (22) for spraying a fluid biochemical agent onto a slide (24) has a main body (52) a plug (56) in the main body (52) and a cap (54) on the main body (52) between which there is a swirl chamber (68) into which fluid passes from the body (52). The fluid enters the swirl chamber (68) such that flow in the chamber (68) is concentric to the chamber axis and thereafter flows from the body (52) through an exit (66), thus minimising damage to the biochemical agent.

6 Claims, 5 Drawing Sheets

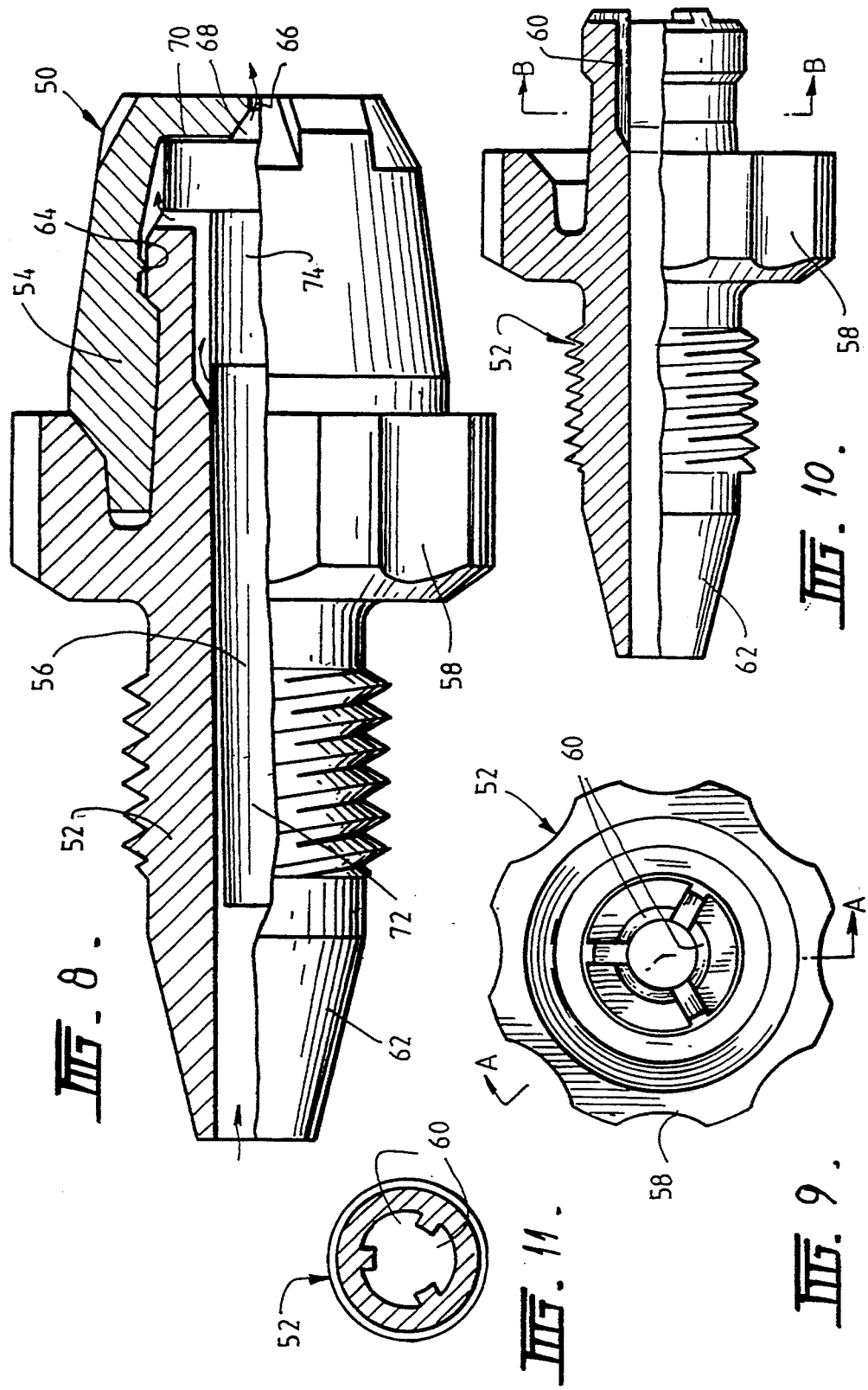

APPARATUS FOR AUTOMATIC TISSUE STAINING FOR IMMUNOHISTOCHEMISTRY

This is a division of application Ser. No. 07/960,358, filed Jan. 19, 1993.

BACKGROUND OF THE INVENTION

This invention relates to immunohistochemistry, and in particular relates to a spray nozzle for apparatus for automatically staining tissue sections, or cell preparations.

Histochemistry is a branch of biochemistry devoted to the study of the chemical composition and structure of animal and plant tissues. It involves the use of microscopic, x-ray diffraction and radioactive tracer techniques in examining the cellular composition and structure of bones, blood, muscle and other animal and vegetable tissues.

Immunohistochemistry is useful for directly viewing the cellular distribution of a molecule (marker) using labelled antibodies or other ligands including nucleic acid probes. Labels include enzymes, radioisotopes and fluorescent molecules. The technique can be applied to whole cells, for example for identification of lymphomas (white blood cell cancers) or to tissue sections, for example for cancer diagnosis.

The specific (or primary) antibody may be labelled directly. Alternatively and more often, a second antibody carrying the label is used to specifically bind to the first. Also, the tissue may require pretreatment to reveal the marker of interest (enzymic) or to remove non-specific effects.

A number of methods have been developed to amplify the visual signal and this may add several steps to the technique. Ultimately, in the case of an enzyme-label a substrate is applied which produces a coloured product at the site of the label. The surrounding tissue is then counterstained to provide contrast. Therefore most protocols for carrying out staining involve a large number of incubations of various time periods, separated by washing to remove spent reagents.

Each operation requires considerable care in the application of small amounts (50 to 200 microliters) of reagents to cover the tissue adequately and also in the washing steps to ensure complete removal of spent reagents and to avoid accidental removal of tissue from the slide. Thus, when a large number of slides are involved the procedure is labour intensive, tedious and can suffer from a lack of reproducibility.

A manual technique currently utilised for staining tissue involves a skilled technician performing all operations manually.

Firstly, glass specimen slides are supported on trays. When staining is carried out above ambient temperature, heating is normally provided using a specially designed temperature-controlled template with provision to allow high humidity.

The slides are washed with a buffer stream from a hand-operated dispensing bottle. The slides are then cleared of liquid by being set vertically to drain, and wiped around the specimen with paper towel material.

The biochemical agent delivery is via a manual pipettor positioned by eye such that the fluid is spread to cover the tissue sample. Chemical reagents with short active lives are manually mixed in vials using standard pipettors.

The control of event sequences and times is performed manually with the aid of a stopwatch and note pads.

It is obvious that such a manual process is inherently inaccurate, time consuming and costly.

There have been prior attempts to automate such a process, and details of such attempts appear hereunder.

(1) Stross, W. P., Jones, M., Mason, D. Y. J. Clin. Pathol. January 1989 42(1) p 106–112 These authors have modified en existing tissue processing instrument (Histokinette E7326; British American Optical Corporation) to carry out immunohistochemical staining of tissues in a semi-automated manner. Slides are placed in racks which are dipped into tanks of reagents which are used repeatedly for up to four months. The method was only applied to the (APAAP) Alkaline phophatase staining method and did not automate the application of primary antibody or substrate.

(2) Brigati, D. J., Budgeon, L. R., Unger, E. R., Koebler, D., Cuomo, C., Kennedy, T., Perdomo, J. M. J. Histotechnol. 11(3), 1988 p 165–183 These authors claim to have developed the first automated method for immunocytochemistry. The method uses a triaxial robotic slide system to move racks of slides between reagents. The slides are paired so that reagents fill the gaps between slides by capillary action. The system is claimed to be able to carry out the complete immunostaining procedure as well as in-situ hybridisation and has been commercialised by Fischer Scientific Co. (U.S.A.).

(3) Stark, E., Faltinat, D., Von der Fecht, R., J. Immunological Methods 107 (1988) p 89–92 These authors have described an instrument in which up to 30 slides are carried on a carousel which can be rotated rapidly to remove reagents. The antibodies or other solutions are piperted onto the slides by standard plastic syringes. This approach has a major disadvantage in that it uses large volumes of expensive reagents and does not automate the primary antibody step.

(4) Mehven, L., Med. Lab. World February 1989 p 45–46 Described a novel coverslip device which is used to create a capillary gap between the slide and coverslip. Reagents are transfered from vials in a carousel to a funnel part of the coverslip using an automatic pipette and an x-slide device. 10 basic method programs can be used to run 20 slides automatically with a variety (up to 9) primary antibodies. The instrument has been commercialised by Shandon Scientific (U.K.) under the "Cadenza" trade name.

(5) Recently Lipshaw (U.S.A.) have released an instrument for the automatic staining of batches of slides by the peroxide technique. The system involves the transfer of a rack of slides between baths of reagents with a robotic arm. The instrument is limited to use for slides undergoing identical methods, is not useful for adding primary antibody and uses large volumes of other reagents.

SUMMARY OF THE INVENTION

It is an object of the present invention to provide improved apparatus for immunohistochemical staining tissue or cell preparations.

It is an object of the present invention to provide an improved device for use in immunohistochemical staining tissue or cell preparations, which device is in the form of a spray nozzle.

The invention provides a spray nozzle for spraying small accurate quantities of fluid, said nozzle including an elongate body having a bore therethrough for passage of said fluid from an inlet end to an outlet end, an end cap having a swirl chamber and a fluid outlet from said swirl chamber, said end cap engaging with the outlet end of said body whereby a space is provided between said outlet end and said swirl chamber, a plug having a head and a spigot extending therefrom, said head being located in said space and said spigot extending along said bore, the combination of said bore and said spigot producing a generally gradual reduction in the annular internal volume of the fluid path from said inlet end to said outlet end to increase fluid flow velocity gradually.

BRIEF DESCRIPTION OF THE DRAWINGS

A preferred embodiment of the invention, will be described in detail hereinafter with reference to the accompanying drawings, in which:

FIG. 8 is a side elevation of a spray nozzle;

FIG. 9 is an end elevation of a spray nozzle body;

FIG. 10 is a section along the lines A—A of FIG. 9;

FIG. 11 is a section along the lines B—B of FIG. 10;

Figure 1:
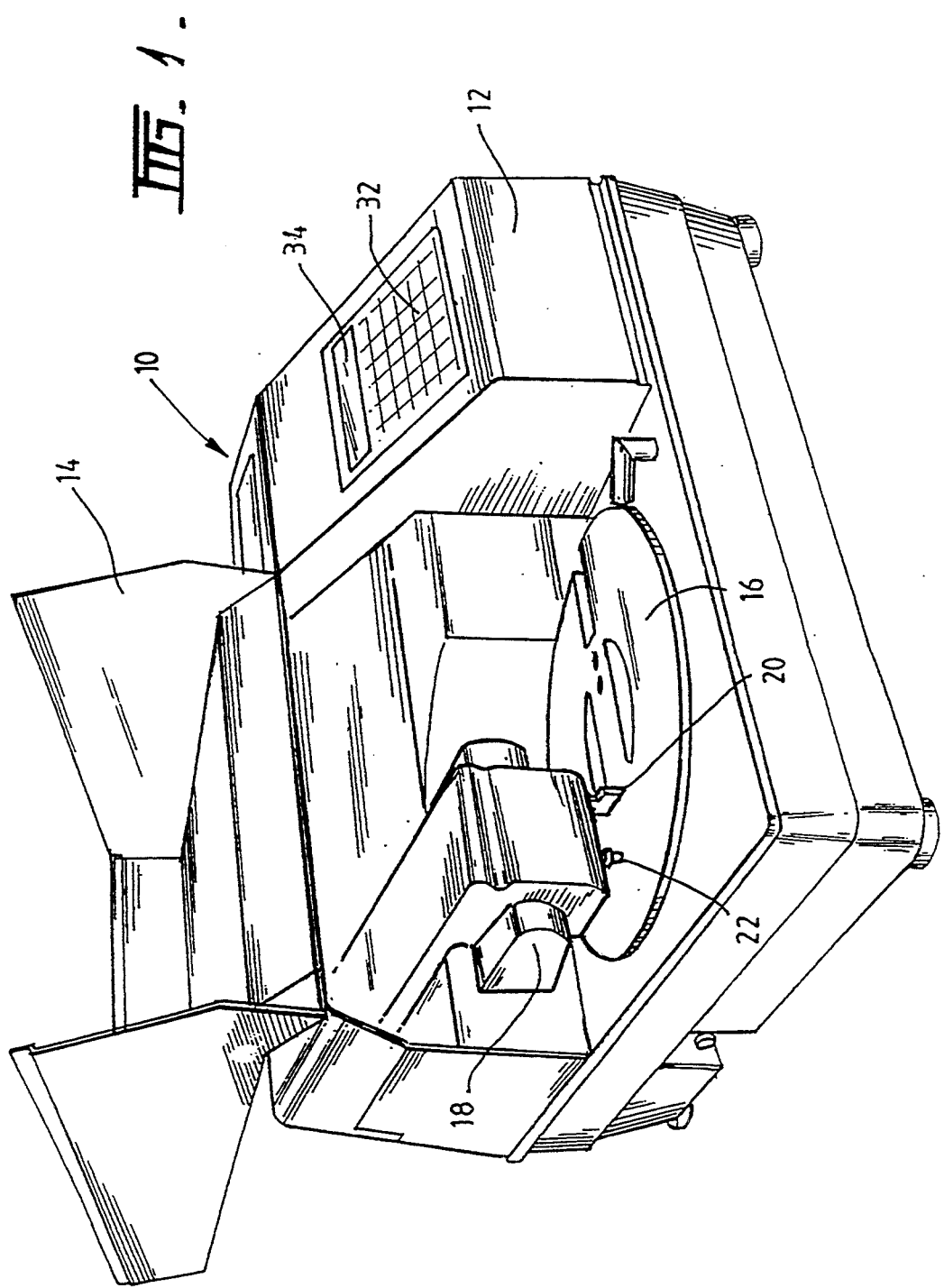
FIG. 1 is a perspective view of automatic tissue staining apparatus.
Figure 2:
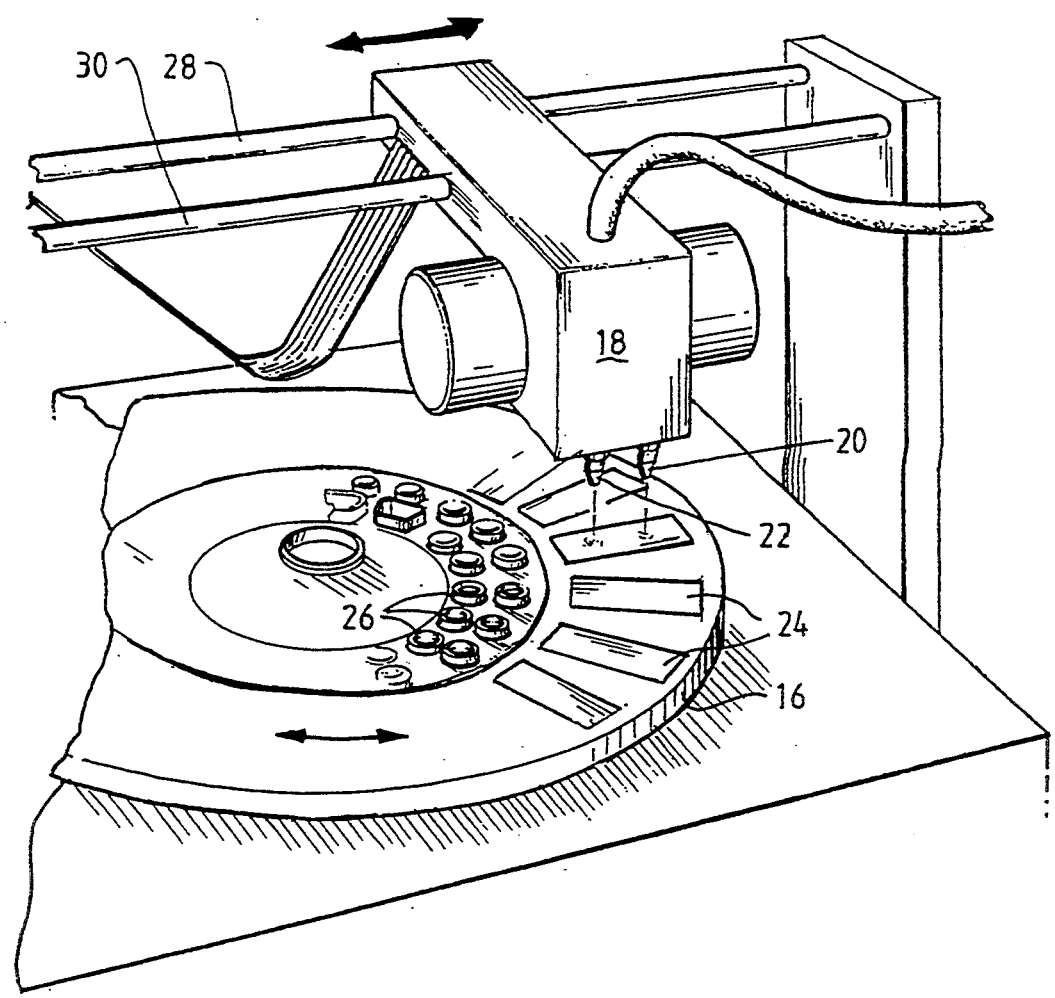
FIG. 2 is a perspective view of a detail of apparatus generally similar to that of FIG. 1.
Figure 3:
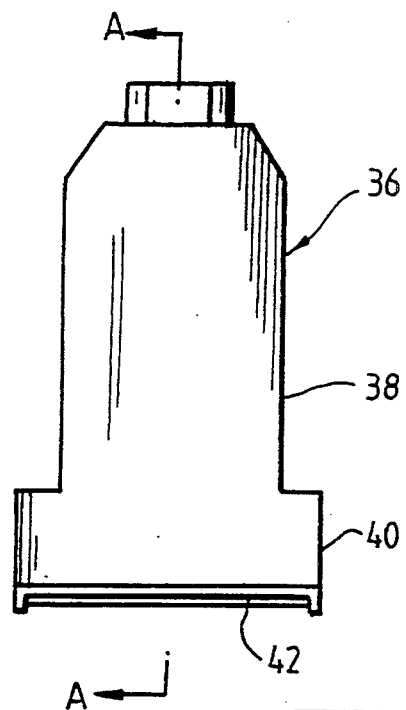
FIG. 3 is a front elevation of a clear nozzle.
Figure 4:
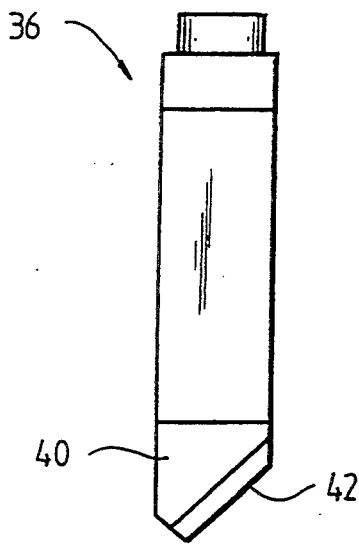
FIG. 4 is a side elevation of the nozzle of FIG. 3.
Figure 5:
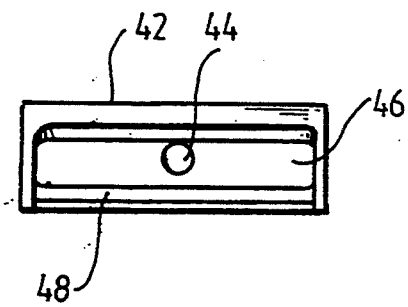
FIG. 5 is a rear elevation of part of the nozzle of FIG. 3.
Figure 6:
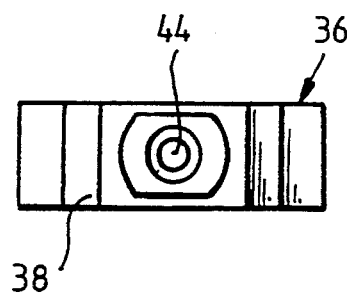
FIG. 6 is an underneath plan view of the nozzle of FIG. 3.
Figure 7:
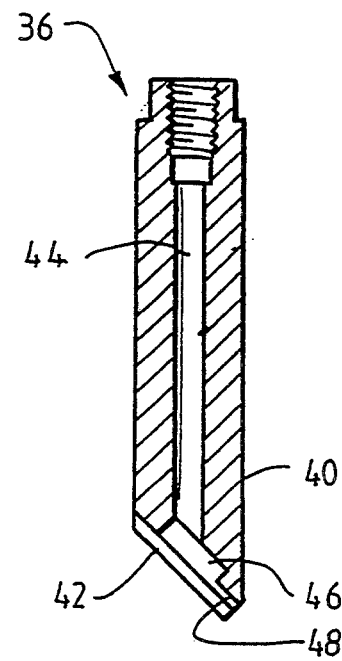
FIG. 7 is a section along the lines A—A of FIG. 3.
Figure 12:
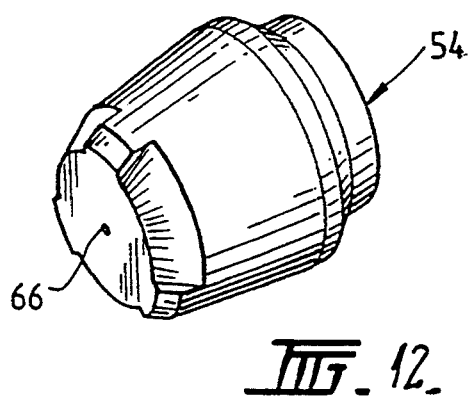
FIG. 12 is a perspective view of a spray nozzle end cap.

Referring firstly to FIGS. 1 and 2, the automatic tissue stainer 10 includes a body 12 having a hinged portion 14 in an open position showing a horizontal carousel 16, a delivery head assembly 18, clear nozzle 20 and spray nozzle 22.

As shown in FIG. 2—which represents a slightly different model to that illustrated in FIG. 1—the carousel 16 is adapted to rotate about a generally vertical axis, and is further adapted to carry slides 24 on a single level surface near its periphery, and reagent or the like containers 26 towards the axis of the carousel 16.

Delivery head assembly 18 is adapted to move across the diameter of carousel 16, on rails 28 and 30, and it can be seen that a combination of rotational movement of the carousel and translational movement of the head 18 enables nozzles 20, 22 to direct material onto any part of any slide 24 or to any container 26. Preferably a third (wash fluid delivery) nozzle is also mounted on head assembly 18, and preferably each nozzle is capable of vertical movement relative to the assembly.

The apparatus 10 enables automatically controlled sequences to be carried out using various electro-mechanical systems (not shown). The apparatus 10 is operated and controlled by a keypad 32 and display 34.

The carousel 16 is adapted to be heated, preferably from beneath and possibly utilising hot air. Preferably, use is made of heated water located beneath the slide, which are located upon supports. Preferably, automatic temperature and control, of the water, is provided.

Head assembly 18 may also include a slide wash facility (not shown) which involves the delivery of a stream of buffer or wash liquid from a dispenser, in a controlled fashion, from the aforementioned third nozzle to a slide 24 located beneath the dispenser on carousel 16. Preferably, the head 18 moves along the slide axis, to evenly distribute the liquid on the slide. Preferably, the buffer liquid is supplied from a pressurised storage bottle with a valved on/off control.

The head assembly 18 also includes a slide clear facility, which is used to clear a slide 24 of liquid dispensed as described in the preceding paragraph. To so clear the slide, the nozzle 36 of FIGS. 3 to 7 inclusive is utilised, which nozzle 36 may take the place of generalised nozzle 20 of FIG. 1.

Clear nozzle 36 includes a body 38 with a widened dispensing end 40 over which is located a plate 42. There is above 44 in body 36, communicating with a plenum 46 in end 40. An exit orifice 48 directs a "curtain" of air onto a slide 24. Preferably, air from a pressurised manifold is supplied to nozzle 36.

Nozzle 36 is moved by head 18 along the axis of slide 24, and the stream or curtain of air from orifice 48 pushes any fluid on the surface of slide 24 along the axis and off the sides and ends of the slide.

Head 18 also includes a biochemical agent delivery facility, using the spray nozzle 50 of FIGS. 8 to 17 inclusive, which nozzle 50 may take the place of generalised nozzle 22 of FIG. 1.

Spray nozzle 50 includes a main body 52, an end cap 54 and a plug 56. Main body 52 has a knurled portion 58 adapted to be used to secure body 52 to end cap 54. Body 52 also has radially extending lugs which define flow-splitting channels 60 and a ferrule seal 62, the latter for connection to a vacuum source, a pipettor or the like for operating the spray nozzle.

End cap 54 has an internal circumferential sealing lip 64 which seals with main body 52. The cap has an axially-located exit orifice, behind which is a swirl chamber 68 tapering towards exit 66.

Figure 13:
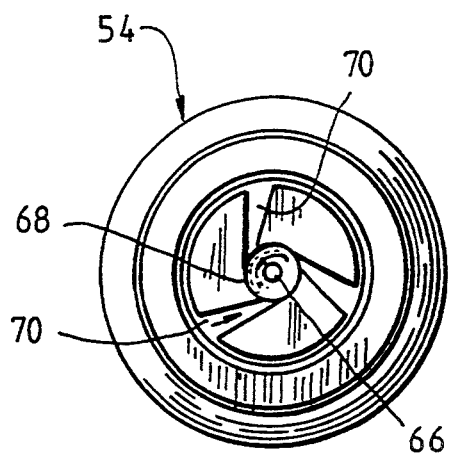
FIG. 13 is a front elevation of the cap of FIG. 13.
Figure 14:
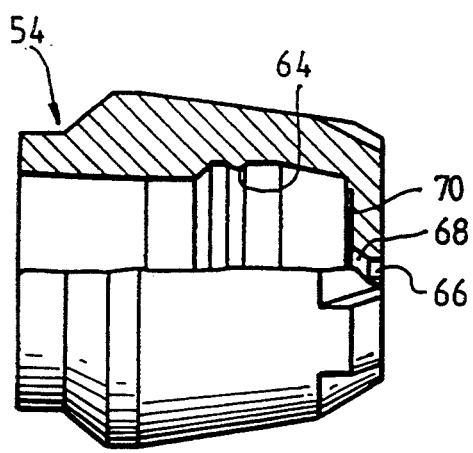
FIG. 14 is a partially sectioned side elevation of the cap of FIG. 13.
Figure 15:
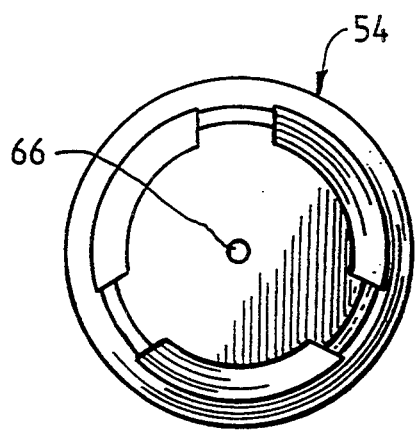
FIG. 15 is a rear elevation of the cap of FIG. 13.
Figure 16:
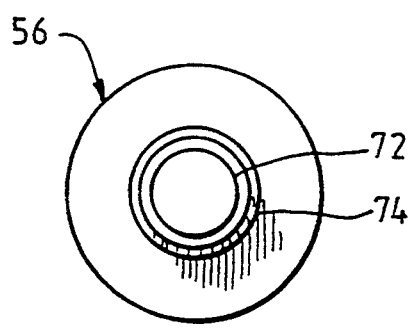
FIG. 16 is an end elevation of a plug.
Figure 17:
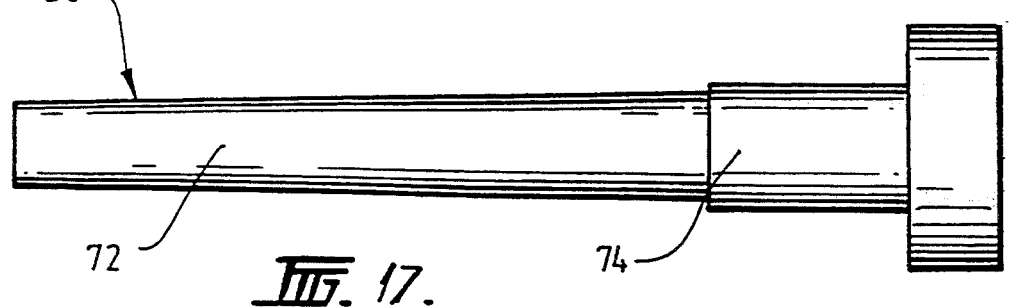
FIG. 17 is a side elevation of the plug of FIG. 16.

In FIG. 13 (rear elevation) is shown tapered channels 70 which acts to direct fluid (see the arrows) into the swirl chamber 68 to ensure that the flow is concentric to the chamber axis.

Plug 56 has a spigot 72 and a locating boss 74.

In the assembled nozzle 50 of FIG. 8, the direction of fluid is shown by arrows. The nozzle 50 achieves a small vortex spray chamber effect where fluid is forced under pressure into a circular chamber (68) in such a manner that the flow is concentric to the axis. The spray exits through central outlet 66.

The structure and operation of the spray nozzle 50 is such that antibodies—as a reagent sub-group—may be sprayed onto a surface without loss of activity.

The proteins in antibodies are susceptible to shear forces normally encountered in conventional spray nozzles. This results in the antibodies being denatured and to consequently lose activity. For that reason, spraying of antibodies has not been considered possible.

It appears that when using the spray nozzle 50, the fluid path is such that antibodies emerge unscathed from the exit 66.

It is preferable to minimise spray head "dead space" and to optimise the fluid velocity and flow so that the correct spray section and pattern are provided to cover an area of a slide 24 from the delivery position. Preferably the area is less than the total area of the slide, more preferably in the range ¼ to ¾ of the total slide area, and more preferably ½ the total slide area, and the nozzle 50 is preferably located between 10 mm and 100 mm above slide 24, more preferably about 30 mm above a slide 24.

Furthermore, it is preferable that the nozzle 50 perform with a total fluid volume per spray of between 50 and 200 microliters. This small volume is selected to cover the slide area with a consistent layer of fluid.

The various parts (52,54,56) of nozzle 50 are preferably formed from injection-moulded plastics material, and the nozzle is preferably connected via ferrule 62 to the delivery conduit of a pipettor delivery head. The pipettor is preferably an electrical/electronic pipettor system (not shown) which acts on a syringe to draw fluid from a container 26 (storage vial) to deliver the fluid via nozzle 50 to slide 24.

The pipettor facilitates the obtention of fluid by a controlled vertical motion whereby it moves down such that the syringe is within the fluid storage vial 26; the pipettor then operates to draw the required amount of fluid into the system; and the syringe moves up in a controlled manner to withdraw from the storage vial 26.

Some chemical agents require mixing just prior to use; they have short active lifetimes after mixing. These items may be mixed by the use of the pipettor system drawing up one agent from its storage vial and dispensing it into the storage vial in which the second agent is held. The mixed solution is then drawn up and dispensed onto the slides as described.

As described earlier, the apparatus 10 provides an automatic tissue-staining or slide washing/drying coating process.

Preferably, there are six modes of operation:

Process Mode: Unit automatically running program.
Load Mode: Operator loading slides/reagents with unit prompt.
Program Mode: Operator setting up a specific protocol program for use in process mode.
Unload Mode: Cycle complete, operator unloads processed slides.
Self Clean Mode: Unit self flushing the working surfaces.
Self Test Mode: Unit running pre-run checks.

The apparatus is capable of performing any combination of the programmed protocols up to a limit of ten. The apparatus is capable of processing up to twenty slides.

Preferably, the apparatus carries a power failure battery back up to enable processing to be satisfactorily shut down at an appropriate stage.

It can be seen that this invention provides apparatus which enables the old manual techniques to be replaced by automatic procedures, operated by a less skilled operator.

We claim:

1. Apparatus for processing tissue samples in immunohistochemistry, said samples being located on slides and said apparatus including slide support means, washing means for dispensing washing fluid onto a said slide, cleaning means for cleaning said slide, and agent dispensing means for dispensing agent onto said sample, said agent dispensing means comprising a spray nozzle, nozzle including:

an elongate body having a bore therethrough for passage of said fluid from an inlet end to an outlet end, an end cap having a swirl chamber and a fluid outlet from said swirl chamber, said end cap engaging with the outlet end of said body whereby a space is provided between said outlet end and said swirl chamber, a plug having a head and a spigot extending therefrom, said head being located in said space and said spigot extending along said bore, the combination of said bore and said spigot producing a generally gradual reduction in the annular internal volume of the fluid path from said inlet end to said outlet end to increase fluid flow velocity gradually such that fluid containing antibodies can be sprayed in a fine spray from said fluid outlet without the antibodies being denatured and losing activity.

2. A spray nozzle for spraying small accurate quantities of fluid, said nozzle including an elongate body having a bore therethrough for passage of said fluid from an inlet end to an outlet end, an end cap having a swirl chamber and a fluid outlet from said swirl chamber, said end cap engaging with the outlet end of said body whereby a space is provided between said outlet end and said swirl chamber, a plug having a head and an elongate spigot extending therefrom, said head being located in said space and said spigot extending along said bore, the combination of said bore and said spigot producing a generally gradual reduction in the annular internal volume of the fluid path from said inlet end to said outlet end to increase fluid flow velocity gradually such that fluid containing antibodies can be sprayed in a fine spray from said fluid outlet without the antibodies being denatured and losing activity.

3. A spray nozzle as defined in claim 2 wherein said body has circumferentially spaced radially extending locating lugs within said bore for locating said spigot centrally within said bore and centrally relative to said end cap, said lugs defining flow-splitting channels therebetween.

4. A spray nozzle as defined in claim 3 wherein fluid flow in said annular internal volume is directed into said swirl chamber by tapered channels in said end cap tangential to said swirl chamber, said channels being narrower towards said swirl chamber.

5. A spray nozzle as defined in claim 4 wherein said fluid outlet is co-axial with the central axis of said swirl chamber and three said tapered channels, equally spaced, are provided to direct said fluid into said swirl chamber.

6. A spray nozzle as defined in claim 5 wherein said end cap is a snap-on fit to the outlet end on said body and interlocks with said outlet end to prevent removal under fluid pressure and a circumferential sealing lip is provided on said end cap, on an internal surface thereof, to sealingly engage with the outer surface of said body.

* * * * *

UNITED STATES PATENT AND TRADEMARK OFFICE
CERTIFICATE OF CORRECTION

PATENT NO.    : 5,425,918

DATED         : June 20, 1995

INVENTOR(S)   : HEALEY et al.

It is certified that error appears in the above-identified patent and that said Letters Patent is hereby corrected as shown below:

On the title page:

Item [30] PCT/AU91/00170 29 April 1991, should be inserted in the Foreign Application Priority Data.

Signed and Sealed this

Fourteenth Day of November, 1995

Attest:

Attesting Officer

BRUCE LEHMAN

Commissioner of Patents and Trademarks